(12) United States Patent
Hildbrand

(10) Patent No.: US 8,153,815 B2
(45) Date of Patent: Apr. 10, 2012

(54) PSEUDOPROLINE DIPEPTIDES

(75) Inventor: Stefan Hildbrand, Gelterkinden (CH)

(73) Assignee: Hoffman-La Roche Inc., Nutley, NJ (US)

( * ) Notice: Subject to any disclaimer, the term of this patent is extended or adjusted under 35 U.S.C. 154(b) by 271 days.

(21) Appl. No.: 12/566,703

(22) Filed: Sep. 25, 2009

(65) Prior Publication Data

US 2010/0087654 A1 Apr. 8, 2010

(30) Foreign Application Priority Data

Oct. 7, 2008 (EP) ..................................... 08165968

(51) Int. Cl.
*C07D 263/06* (2006.01)
(52) U.S. Cl. ..................................................... 548/215
(58) Field of Classification Search ........................ None
See application file for complete search history.

(56) References Cited

U.S. PATENT DOCUMENTS 6,790,935 B1 9/2004 Mutter et al.

FOREIGN PATENT DOCUMENTS

| WO | WO 00/46239 | 8/2000 |
| WO | WO 2008/000641 | 1/2008 |

OTHER PUBLICATIONS

Wohr T. et al, *J. Am. Chem. Soc.*, (1996) 118:39 pp. 9218-9227, XP-00244730.

Wohr T. et al, *Tetrahedron Letters*, (1995) vol. 36:22, pp. 3847-3848, XP004027998.

*Primary Examiner* — Kamal Saeed
(74) *Attorney, Agent, or Firm* — George W. Johnston; Dennis P. Tramaloni

(57) ABSTRACT

Disclosed is a process for the manufacture of pseudo proline dipeptides of the formula

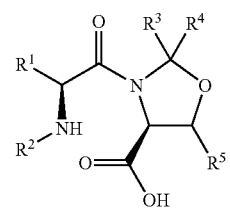

I wherein $R^1$ is a side chain of an alpha amino acid, $R^2$ is an amino protecting group and $R^3$ and $R^4$ are independently selected from hydrogen or $C_{1-4}$-alkyl, $R^5$ is hydrogen or methyl starting from an amino acid derivative of the formula

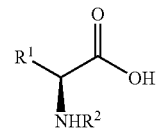

II wherein $R^1$ and $R^2$ are as above.

Pseudo proline dipeptides can be used as reversible protecting groups for Ser, Thr and Cys and thus are versatile tools in peptide chemistry.

20 Claims, No Drawings

PSEUDOPROLINE DIPEPTIDES

PRIORITY TO RELATED APPLICATIONS

This application claims the benefit of European Patent Application No. 08165968.2, filed Oct. 7, 2008, which is hereby incorporated by reference in its entirety.

BACKGROUND OF THE INVENTION

A synthetic approach to pseudoproline dipeptides is published in PCT Publication WO 2008/000641, wherein access to the compound of formula I is accomplished via an ammonium salt intermediate of formula

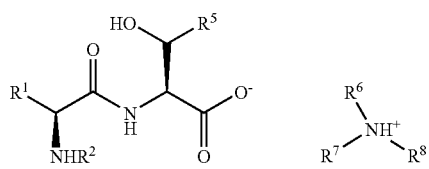

wherein further $R^1$, $R^2$, $R^5$, $R^6$, $R^7$ and $R^8$ are as defined in PCT 2008/000641.

One major disadvantage of the PCT 2008/000641 approach is the need to purify the dipeptide by isolation of its ammonium salt intermediate, which prior to the ring closure has to be liberated to the dipeptide. Accordingly this synthesis is less suitable for application on a technical or commercial scale.

The present invention overcomes the disadvantages of the PCT 2008/000641 approach and instead provides a short and technically feasible synthesis of the pseudo proline dipeptides of formula I which allows for obtaining the product with a high yield.

SUMMARY OF THE INVENTION

The invention generally relates to a novel process for the manufacture of pseudoproline dipeptide compounds, specifically compounds of formula

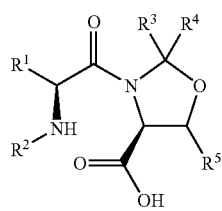

wherein $R^1$ is a side chain of an alpha amino acid, $R^2$ is an amino protecting group and $R^3$ and $R^4$ are independently selected from hydrogen, with the proviso that not both $R^3$ and $R^4$ are hydrogen or $C_{1-4}$-alkyl, $R^5$ is hydrogen or methyl, comprising converting an amino acid derivative of the formula

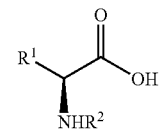

wherein $R^1$ and $R^2$ are as above, with serine or threonine into the dipeptide of formula

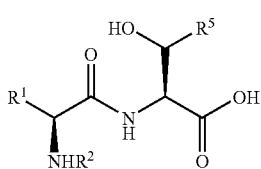

using a water soluble carbodiimide as activating agent, and effecting the ring closure of the dipeptide of formula III with a compound of formula wherein $R^3$ and $R^4$ are independently selected from hydrogen or $C_{1-4}$-alkyl, with the proviso that not both $R^3$ and $R^4$ are hydrogen and $R^{9a}$ and $R^{9b}$ independently are $C_{1-4}$-alkyl, in the presence of an acidic catalyst.

DETAILED DESCRIPTION OF THE INVENTION

The invention generally relates to a novel process for the manufacture of pseudoproline dipeptide compounds, specifically compounds of formula The pseudo proline dipeptides of formula I can be used as reversible protecting groups for Ser, Thr, and Cys and prove to be versatile tools for overcoming some intrinsic problems in the field of peptide chemistry [JACS 1996, 118, 9218-9227], The presence of ΨPro within a peptide sequence results in the disruption of β-sheet structures considered as a source of intermolecular aggregation. The resulting increased solvation and coupling kinetics in peptide assembly such as Fmoc solid phase peptide synthesis facilitates chain elongation especially for peptides containing "difficult sequences".

More specifically, the invention relates to a novel process for the manufacture of a compound of formula

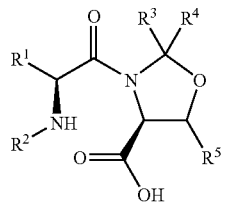

I wherein $R^1$ is a side chain of an alpha amino acid, $R^2$ is an amino protecting group and $R^3$ and $R^4$ are independently selected from hydrogen, with the proviso that not both $R^3$ and $R^4$ are hydrogen or $C_{1-4}$-alkyl, $R^5$ is hydrogen or methyl, comprising
converting an amino acid derivative of the formula

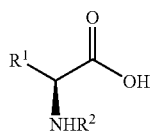

II wherein $R^1$ and $R^2$ are as above, with serine or threonine into the dipeptide of formula

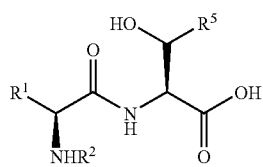

III using a water soluble carbodiimide as activating agent, and effecting the ring closure of the dipeptide of formula III with a compound of formula

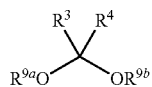

IV wherein $R^3$ and $R^4$ are independently selected from hydrogen or $C_{1-4}$-alkyl, with the proviso that not both $R^3$ and $R^4$ are hydrogen and $R^{9a}$ and $R^{9b}$ independently are $C_{1-4}$-alkyl, in the presence of an acidic catalyst.

DEFINITIONS

All references, publications and art cited herein are hereby incorporated by reference in their entirety.

The term "serine" encompasses serine in either its L- or D-configuration, as well as racemate or in various mixtures of its isomers. Preferably the L-configuration is used.

The term "threonine" encompasses threonine in either its L- or D-configuration, as well as racemate or in various mixtures of its isomers. Preferably the L-configuration is used.

The term "$C_{1-4}$-alkyl" refers to a branched or straight-chain monovalent saturated aliphatic hydrocarbon radical of one to four carbon atoms. This term is further exemplified by radicals as methyl, ethyl, n-propyl, isopropyl, n-butyl, s-butyl and t-butyl.

The term "side chain of an amino acid" used for the substituent $R^1$ particularly refers to side chains of the alpha amino acids selected from valine, leucine, isoleucine, methionine, phenylalanine, asparagine, glutamine, glutamic acid, histidine, lysine, arginine, aspartic acid, alanine, serine, threonine, tyrosine, tryptophan, cysteine, glycine, aminoisobutyric acid and proline. Preferably, $R^1$ is a side chain of valine, leucine, isoleucine, phenylalanine, asparagine, glutamine, glutamic acid, lysine, aspartic acid, alanine, serine, threonine, tyrosine and tryptophan. In a more preferred embodiment $R^1$ stands for a side chain of serine or threonine.

It is understood that in side chains of amino acids which carry a hydroxy group the hydroxy group is optionally protected by a hydroxy protecting group. The term "hydroxy protecting group" refers to any substituents conventionally used to hinder the reactivity of the hydroxy group. Suitable hydroxy protecting groups are described in Green T., "Protective Groups in Organic Synthesis", Chapter 1, John Wiley and Sons, Inc., 1991, 10-142. Suitable hydroxy protecting groups are t-butyl, benzyl, TBDMS or TBDPS. A preferred hydroxy protecting group is t-butyl.

In side chains that carry additional amino groups the amino group is optionally protected by an amino protecting group. The term "amino protecting group" refers to any substituents conventionally used to hinder the reactivity of the amino group. Suitable amino protecting groups are described in Green T., "Protective Groups in Organic Synthesis", Chapter 7, John Wiley and Sons, Inc. 1991, 309-385. Suitable amino protecting groups as defined under $R^2$ should withstand under acidic conditions. Preferably Fmoc, Z, Moz, Troc, Teoc or Teoc more preferably Fmoc is used.

Abbreviations used in the description and the claims are as outlined in the table below:

| | |
|---|---|
| Fmoc | 9-Fluorenylmethoxycarbonyl |
| Z | Benzyloxycarbonyl |
| tBu | t-butyl |
| Moz | p-Methoxybenzyloxycarbonyl |
| Troc | 2,2,2-Trichloroethoxycarbonyl |
| Teoc | 2-(Trimethylsilyl)ethoxycarbonyl |
| Voc | Vinyloxycarbonyl |
| TBDMS | t-Butyldimethylsilyl ether |
| TBDPS | t-Butyldiphenylsilyl ether |
| HOBt | 1-Hydroxybenzotriazole |
| HOSu | N-Hydroxysuccinimide |
| EAC | 1-Ethyl-3-(4-azonia-4,4-dimethylpentyl)-carbodiimide (iodide) |
| EDC | (3-Dimethylamino-propyl)-ethyl-carbodiimide (hydrochloride) |

DETAILED DESCRIPTION

The process for the manufacture or, or method of making, a compound of formula I

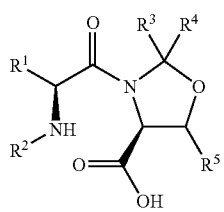

I wherein R¹ is a side chain of an alpha amino acid, R² is an amino protecting group and R³ and R⁴ are independently selected from hydrogen or $C_{1-4}$-alkyl, R⁵ is hydrogen or methyl, comprises Step a)
In step a) the process comprises converting an amino acid derivative of formula

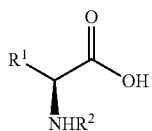

II wherein R¹ and R² are as above, with serine or threonine into the dipeptide of formula

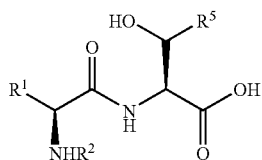

III using a water soluble carbodiimide as activating agent. The process of step (a) thus comprises an activation of the amino acid derivative and then the coupling of the activated amino acid derivative with serine or threonine.

The amino acid derivatives of formula II are as a rule commercially available compounds. Suitable amino acid derivatives of formula II according to the preferences given for R¹ and R² are Fmoc-L-Ser (tBu)-OH, or Fmoc-L-Thr (tBu)-OH.

Suitable water soluble carbodiimide activating agents are EDC or EAC or salts thereof, preferably the hydrochloride salt of EDC.

Preferably, the water soluble carbodiimide activating agent is applied together with a further activating agent selected from HOSu or HOBt.

A preferred activating agent is EDC.HCl/HOSu. In such a preferred embodiment, the EDC is typically applied in an amount of 1.0 to 1.5 equivalents and the HOSu is typically applied in an amount of 1.0 to 1.5 equivalents, as related to one equivalent of the amino acid derivative of formula II.

Preferably the activation reaction is also performed in the presence of a suitable organic solvent, such as ethylacetate, N,N-dimethylformamide, acetone or tetrahydrofuran, preferably tetrahydrofuran and/or N,N-dimethylformamide. Preferably, the activation reaction of step (c) is performed at a temperature of −10° C. to 25° C.

The coupling with serine or threonine, preferably with L-serine or L-threonine, is then performed at a temperature of −10° C. to 25° C. in the presence of an inorganic base, wherein the coupling takes place by adding a solution of the activated ester obtained from the activation reaction to an aqueous suspension of serine or threonine and the inorganic base.

Suitable inorganic bases are alkali carbonates such as lithium-, sodium- or potassium-carbonates or hydroxides or mixtures thereof. Preferred inorganic bases are lithium carbonate and for lithium hydroxide, with mixtures of lithium carbonate and lithium hydroxide, being more preferred. Preferably, the inorganic base applied stoicheometrically related to serine or threonine. Preferably the ratio of serine or threonine to amino acid derivative of formula II is usually selected in the range of 1.5 to 4.0 to 1, preferably 2.0 to 3.0 to 1.

The pH of the reaction mixture during conversion is preferably maintained in a range of 7.5 to 9.5.

After completion of the conversion the reaction mixture is acidified with a mineral acid. Suitable mineral acids are aqueous sulfuric acid or aqueous HCl, preferably aqueous sulfuric acid.

The dipeptide of formula III can be isolated following methods known to the skilled in the art. In a preferred embodiment of the invention the dipeptide of formula III is directly, without its isolation, used in process step b).

Step b)
Step b) comprises effecting the ring closure of the dipeptide of formula III with a compound of formula

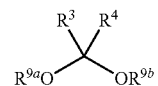

IV wherein $R^3$, $R^4$, $R^{9a}$ and $R^{9b}$ are as above, in the presence of an acidic catalyst.

Preferably the compounds of formula IV are used in an amount of 6.0 to 16.0 equivalents, preferably 7.0 to 12.0 equivalents in relation to the di-peptide obtained in step b). Preferably the compound of formula IV is 2,2-dimethoxypropane. In a more preferred embodiment the 2,2-dimethoxypropane is continuously added to the reaction mixture while in parallel the methanol generated is continuously distilled of.

The reaction temperature for the ring closure of step (b) is usually maintained in the range of 15° C. to 35° C., preferably between 20° C. and 30'C.

Suitable acidic catalysts are selected from methane sulfonic acid, (+) camphor-10-sulfonic acid, p-toluenesulfonic acid or pyridinium p-toluenesulfonate, while methane sulfonic acid is preferred. The acidic catalyst is usually applied in an amount of 0.05 to 0.30 equivalents, preferably 0.08 to 0.15 equivalents in relation to the dipeptide of formula III obtained in step b).

The organic solvent ideally applied for the conversion in step b) is substantially freed of water. Suitable solvents are toluene or tetrahydrofuran or mixtures thereof.

The compound of formula I then may be isolated and obtained from the reaction mixture by methods known to the skilled in the art. A preferred isolation procedure comprises extracting the reaction mixture with water, while maintaining a pH in the range of 7.0 to 9.0, preferably in the range of 7.5 to 8.5.

extracting the water phase with an organic, water immiscible solvent, while maintaining a pH in the range of 5.5 to 6.0, preferably in the range of 5.5 to 5.7.

isolating the target product of formula I from the organic phase and optionally by crystallizing the target product of formula I in an organic solvent.

The adjustment of the pH in step i) of the isolation procedure can happen with a common aqueous buffer e.g. with an aqueous sodium bicarbonate solution, while the pH in step ii) can be adjusted by using an aqueous solution of a mineral acid e.g. with aqueous sulfuric acid.

The organic, water immiscible solvent is preferably toluene.

Isolation in step iii) usually happens by partial evaporation of the organic solvent, whereafter the target product may further be purified by crystallization in a suitable organic solvent, for example a mixture of toluene, isopropanol and heptane.

The following examples serve to illustrate the invention in more detail. The examples are not however intended to limit the scope of the invention in any manner.

EXAMPLES

Synthesis of (S,S)-3-[3-tert-butoxy-2-(9H-fluoren-9-yl-methoxycarbonylamino)-propionyl]-2,2-dimethyl-oxazolidine-4-carboxylic acid

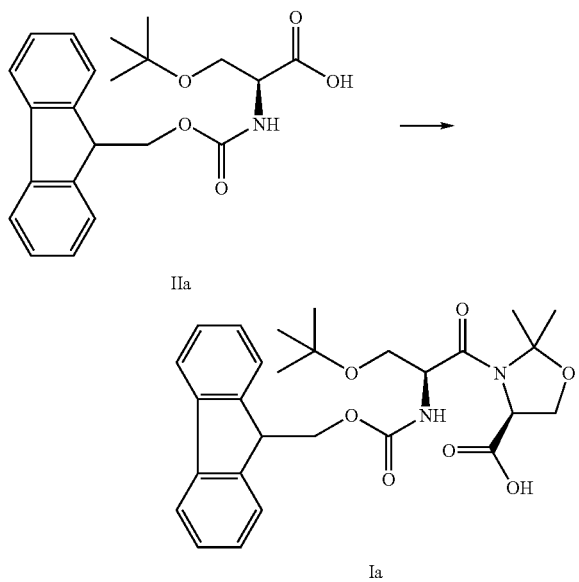

Example 1

A solution of 16.1 g N-hydroxysuccinimide and 40.0 g Fmoc-L-Ser(tBu)-OH in 200 mL of THF was added at 20° C. within 30 to 60 minutes to a suspension of 26.0 g 1-(3-Dimethylaminopropyl)-3-ethylcarbodiimide hydrochloride in 80 mL DMF and 80 mL THF. The resulting mixture was stirred at ambient temperature for 4 hours and then added within 30 to 45 minutes to a pre-cooled (−5° C.) suspension of 8.75 g lithium hydroxide monohydrate, 6.1 g lithium carbonate and 33.2 g L-Serine in 240 g of water. The resulting mixture was allowed to warm to room temperature within 30 minutes and then stirred at this temperature for another hour. The mixture was then cooled to −5° C. and the pH was adjusted from 8.5 to 2.0-2.5 with approx. 150 g of sulfuric acid (20% in water). The biphasic mixture was allowed to warm to room temperature and the lower aqueous layer was then separated. The aqueous layer was extracted with 200 mL of toluene. The combined organic layers were diluted with 150 mL of toluene and then washed with 5×150 mL of water. From the organic layer water was removed by azeotropic distillation with toluene and THF. The water free (<0.05%) toluene/THF solution (approx. 500 mL) was treated with 1.00 g methanesulfonic acid. To the mixture was added within 6 to 10 hours a solution of 100 g of 2,2-dimethoxypropane in 660 mL toluene. During the entire dosing volatiles were distilled off under reduced pressure (80-30 mbar) and at a temperature of 20 to 28° C., keeping the reaction volume (at approximately 600 mL) constant. After complete addition, the mixture was concentrated to a final volume of approx. 500 mL and then treated with 1.35 g triethylamine. Water (50 mL) was added and the layers were separated. The organic layer was treated with 250 g of sodium bicarbonate (5% in water). The biphasic mixture (pH ~7.5) was heated to 35-40° C. and stirred at this temperature for 30 to 45 minutes. The layers were separated and the organic layer was extracted with 3×70 g of sodium bicarbonate (5% in water). The combined product containing aqueous layers were treated at 35-40° C. with 360 mL of toluene and the pH was adjusted to 5.5 by the drop wise addition of approximately 50 g of sulfuric acid (20% in water). The aqueous layer was separated and the organic layer washed with 2×50 g of water. The resulting organic layer was cooled to ambient temperature and diluted with 100 mL, of water. The pH was adjusted to 4 by the addition of a few drops of sulfuric acid (20% in water). The lower aqueous layer was removed and the organic layer washed with 2×80 g of water. The organic layer was concentrated to dryness. The residue was treated with 400 mL of isopropanol and the resulting solution was concentrated to dryness. The residue was diluted with 90 mL isopropanol and 90 mL heptane and the mixture was heated to 50° C. to achieve a clear solution. 400 mL of heptane were added within 3 to 4 hours. The mixture was then cooled to −10° C. within 13-16 hours and the resulting suspension stirred at this temperature for at least 4 hours. The crystals were filtered off, washed with 80 mL of pre-cooled heptane and dried at 40-50° C./<30 mbar to afford 31.6 g (60%) of (S,S)-3-[3-tert.-butoxy-2-(9H-fluoren-9-yl-methoxycarbonylamino)-propionyl]-2,2-dimethyl-oxazolidine-4-carboxylic acid as colorless crystals with a HPLC assay of 99.0% (m/m).

Example 2

A solution of 16.1 g N-hydroxysuccinimide and 40.0 g Fmoc-L-Ser(tBu)-OH in 200 mL of THF was added at 20° C. within 30 to 60 minutes to a suspension of 26.0 g 1-(3-Dimethylaminopropyl)-3-ethylcarbodiimide hydrochloride in 80 mL DMF and 80 mL THF. The resulting mixture was stirred at ambient temperature for 4 hours and then added within 30 to 60 minutes to a pre-cooled (−5° C.) suspension of 8.75 g lithium hydroxide monohydrate, 6.1 g lithium carbonate and 33.2 g L-Serine in 270 g of water. The resulting mixture was allowed to warm to room temperature within 30 minutes and then stirred at this temperature for another hour. The mixture was then cooled to −5° C. and the pH was adjusted to 2.5 with 137 g of sulfuric acid (20% in water). The biphasic mixture was allowed to warm to room temperature and the lower aqueous layer was then separated. The aqueous layer was extracted with 210 mL of toluene. The combined organic layers were diluted with 100 mL of toluene and then washed with 5×130 mL of water. From the organic layer water was removed by azeotropic distillation with toluene and THF. The resulting toluene/THF solution (approx. 550 mL) was then treated with 1.00 g methanesulfonic acid. To the mixture was then added within 8 to 10 hours a solution of 134 g of 2,2-dimethoxypropane in 1040 mL of toluene. During the entire dosing volatiles were distilled off under reduced pressure (80-30 mbar) and at a temperature of 25 to 32° C., keeping the reaction volume (at approximately 600 mL) constant. After complete addition, the mixture was concentrated to a final volume of approx. 500 mL. The reaction mixture was treated with 250 g of sodium bicarbonate (5% in water). The biphasic mixture was heated to 35-40° C. and stirred at this temperature for 15 minutes. The layers were separated and the organic layer was extracted with 100 g of sodium bicarbonate (5% in water). The combined product containing aqueous layers were washed with toluene (150 mL). The aqueous layer was treated at 35-40° C. with 300 mL of toluene and the pH was adjusted to 5.7 by the drop wise addition of approximately 45 g of sulfuric acid (20% in water). The aqueous layer was then separated and the organic layer washed with 3×80 g of water. The resulting product containing organic layer was treated with 80 mL of water. The pH was adjusted to 4 by the addition of a few drops of sulfuric acid (20% in water). The lower aqueous layer was removed and the organic layer washed with 2×80 g of water. The organic layer was concentrated to a residual volume of approximately 170 mL. The mixture was heated to 55-60° C. and isopropanol (15 mL) was added. The resulting clear solution was treated at 55-60° C. within 2-4 hours with 300 mL of heptane. The resulting suspension was cooled to 0° C. within 10 hours and stirred at this temperature for 3 hours. The crystals were filtered off, washed with 100 mL of pre-cooled heptane and dried at 50° C./<30 mbar to afford 33.6 g (63%) of (S,S)-3-[3-tert.-butoxy-2-(9H-fluoren-9-yl-methoxycarbonylamino)-propionyl]-2,2-dimethyl-oxazolidine-4-carboxylic acid as colorless crystals with a HPLC assay of 99.4% (m/m).

The invention claimed is:
1. A process for the manufacture of a compound of formula

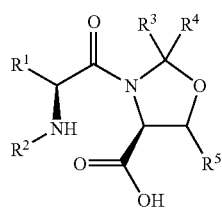

wherein $R^1$ is a side chain of an alpha amino acid, $R^2$ is an amino protecting group and $R^3$ and $R^4$ are independently selected from hydrogen or $C_{1-4}$-alkyl, with the proviso that not both $R^3$ and $R^4$ are hydrogen, $R^5$ is hydrogen or methyl, comprising
a) converting an amino acid derivative of the formula

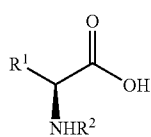

wherein $R^1$ and $R^2$ are as above, with serine or threonine into the dipeptide of formula

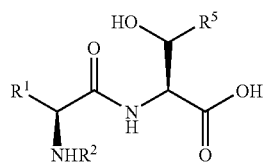

using a water soluble carbodiimide as activating agent, without isolating or crystallizing the dipeptide of formula III and
b) effecting the ring closure of the dipeptide of formula III with a compound of formula

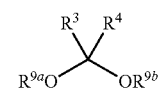

wherein $R^3$ and $R^4$ are independently selected from hydrogen or $C_{1-4}$-alkyl, with the proviso that not both $R^3$ and $R^4$ are hydrogen, and $R^{9a}$ and $R^{9b}$ independently is $C_{1-4}$-alkyl, in the presence of an acidic catalyst.
2. The process of claim 1, wherein $R^1$ is a side chain selected from valine, leucine, isoleucine, methionine, phenylalanine, asparagine, glutamine, glutamic acid, histidine, lysine, arginine, aspartic acid, alanine, serine, threonine, tyrosine, tryptophan, cysteine, glycine, aminoisobutyric acid and proline.
3. The process of claim 1, wherein $R^2$ is selected from Fmoc, Z, Moz, Troc, Teoc and Voc.
4. The process of claim 1, wherein the water soluble carbodiimide is EDC or a salt thereof.
5. The process of claim 4, wherein EDC or a salt thereof is applied together with HOSu.
6. The process of claim 1, wherein the ratio serine or threonine to the amino acid derivative of formula II is in the range of 1.5 to 4.0 to 1.
7. The process of claim 1, wherein the conversion in step a) is performed in the presence of an inorganic base.
8. The process of claim 7, wherein the inorganic base is selected from an alkali carbonate or an alkali hydroxide and from mixtures thereof.
9. The process of claim 1, wherein the conversion in step a) is performed at a pH in the range of 7.5 to 9.5.
10. The process of claim 1, wherein the conversion in step a) is performed at a temperature in the range of −10° C. to 25° C.
11. The process of claim 1, wherein the reaction mixture, after the conversion in step a), is acidified with a mineral acid.
12. The process of claim 1, wherein the dipeptide of formula III is directly obtained in step c), without being isolated, used in process step b).
13. The process of claim 1, wherein the compound of formula IV is 2,2-dimethoxypropane.
14. The process of claim 13, wherein 2,2-dimethoxypropane is continuously added to the reaction mixture while in parallel the methanol generated is continuously distilled of.
15. The process of claim 1, wherein the acidic catalyst for the ring closure in step b) is selected from methane sulfonic acid, (+) camphor-10-sulfonic acid, p-toluenesulfonic acid, pyridinium p-toluenesulfonate.
16. The process of claim 15, wherein the ring closure in step b) is effected in the additional presence of toluene or tetrahydrofuran or of mixtures thereof.

17. The process of claim 1, wherein the ring closure in step b) is performed at a temperature in the range of 15° C. to 35° C.

18. The process of claim 1, wherein the target compound of formula I is isolated by a work up procedure, comprising a) extracting the reaction mixture with water, while maintaining a pH in the range of 7.0 to 9.0;

b) extracting the water phase with an organic, water immiscible solvent, while maintaining a pH in the range of 5.5 to 6.0; and c) isolated the target compound of formula I from the organic phase, crystallizing the target compound of formula I in an organic solvent.

19. The process of claim 18, wherein the organic, water immiscible solvent is toluene.

20. The process of claim 18, wherein the target compound is further crystallized in an organic solvent, wherein the organic solvent is a mixture of toluene, isopropanol and heptane.

* * * * *